United States Patent [19]

Mitsumaki et al.

[11] Patent Number: 4,696,183
[45] Date of Patent: Sep. 29, 1987

[54] METHOD AND APPARATUS OF FLOW ANALYSIS

[75] Inventors: Hiroshi Mitsumaki; Naoya Ono; Isao Shindo; Nobuyoshi Takano, Katsuta, all of Japan

[73] Assignee: Hitachi, Ltd., Tokyo, Japan

[21] Appl. No.: 834,806

[22] Filed: Feb. 28, 1986

[30] Foreign Application Priority Data

Mar. 1, 1985 [JP] Japan .................................. 60-40911

[51] Int. Cl.⁴ ..................... G01N 33/49; G01N 27/46; G01N 27/56
[52] U.S. Cl. ..................................... 73/19; 73/863.01; 73/864.85; 204/400; 204/402; 204/409; 204/1 T
[58] Field of Search ........... 73/864.85, 864.87, 863.01, 73/19; 204/409, 411, 435, 401, 422, 1 T, 1 Y, 415, 402, 400

[56] References Cited

U.S. PATENT DOCUMENTS

| 3,424,557 | 1/1969 | Skeggs | 73/863.01 X |
| 3,649,204 | 3/1972 | Farr | 73/864.85 X |
| 3,960,498 | 6/1976 | Zindler et al. | 204/411 X |
| 3,963,440 | 6/1976 | Stein et al. | 204/411 X |
| 3,969,209 | 7/1976 | Mueller | 204/409 X |
| 3,997,420 | 12/1976 | Buzza | 204/411 |
| 4,172,770 | 10/1979 | Semersky et al. | 204/409 X |
| 4,531,088 | 7/1985 | Czaban et al. | 204/411 X |

FOREIGN PATENT DOCUMENTS

| 39185 | 4/1978 | Japan | 73/863.01 |
| 204364 | 11/1983 | Japan | 73/863.01 |

Primary Examiner—Tom Noland
Attorney, Agent, or Firm—Antonelli, Terry & Wands

[57] ABSTRACT

A flow path in a flow analyzing apparatus is branched into two or more branch flow paths. In one of the branch flow paths, a flow path blockage detector and an electrolyte measuring electrode are disposed, and in the other branch flow path, a gas measuring electrode is disposed. When a liquid sample is introduced into the flow paths from a sampling nozzle of the common flow path, the blockage detector detects whether a blockage is occuring. If the blockage is detected, the blockage is removed by feeding a cleaning fluid into the common flow path in a direction opposite to the flow of the sample. Following this, the sample is introduced into the other branch flow path. By this operation, the pressure in the other branch flow path is not reduced abnormally, and thus normal operation of the gas measuring electrode can be maintained.

14 Claims, 2 Drawing Figures

METHOD AND APPARATUS OF FLOW ANALYSIS

BACKGROUND OF THE INVENTION

The present invention relates to a method and apparatus of flow analysis, and, in particular, to an analyzing method and apparatus in which by introducing a liquid sample into a flow path in the apparatus, the items to be analyzed with respect to the sample flowing in the flow path are measured by a measuring electrode.

In, for example, U.S. Pat. No. 4,452,682, a flow analysis arrangement is provided wherein a plurality of measuring electrodes are arranged along a flow path in which a sample is flowing, and items to be analyzed including gas components, electrolyte, urea, nitrogen, etc., contained in blood are sequentially measured. A pump for transferring the blood sample through the flow path is disposed downstream of the measuring electrodes. As a result, when the flow path is blocked at the entry port for the sample, or a phenomenon of blockage occurs, the pressure within the flow path is reduced. The abnormal pressure drop in the flow path adversely affects the measuring electrodes. In particular, when an oxygen measuring electrode is of the Clark type and when a carbon dioxide measuring electrode is of the Severinghaus type, measured values are affected to a great extent due to the pressure drop.

For example, the carbon dioxide measuring electrode includes an inner electrode, an inner electrolyte solution, and a gas permeable membrane. When this measuring electrode is disposed in the flow path in which the sample is flowing, only the gas permeable membrane is interposed between the flow path and the inner electrolyte solution. Accordingly, the tension of the gas permeable membrane is varied due to a change in pressure within the flow path, and consequently, the accuracy in measurement is degraded.

SUMMARY OF THE INVENTION

An object of the present invention is to provide a method and apparatus in which the measuring electrode which is apt to be affected by a pressure change can be operated in a normal pressure environment.

Another object of the present invention is to provide a method and apparatus in which the measured value obtained by the measuring electrode is not substantially affected by a blockage of the flow path.

A method for implementing the present invention includes a step of introducing a liquid sample into a flow path of an analyzing apparatus from a sample introducing section; a step of measuring whether the sample has reached within a predetermined time a position of a sample liquid detector disposed in a first branch flow path branched from a common flow path; a step of cleaning the common flow path with a cleaning fluid when the sample has not reached the position of the detector within the predetermined time; and a step of introducing the sample into a second branch flow path having a particular measuring electrode disposed therein after cleaning the common flow path, and measuring items to be analyzed.

In a preferred embodiment of the present invention, in the step of measuring the items to be analyzed, the sample is brought into contact with the particular measuring electrode, and after a reference liquid is supplied to a reference electrode, a potential or current caused in the particular measuring electrode is measured.

An apparatus for implementing the present invention includes a common flow path provided with a sample introducing nozzle; a plurality of branch flow paths connected to the common path; means disposed in a first branch flow path for detecting blockage of the flow path; means for removing the blockage by cleaning the common flow path when the blockage of the flow path is detected by the detecting means; a measuring electrode disposed in a second branch flow path, said measuring electrode being apt to be affected by a pressure change in the flow path; and means for introducing the sample into the second branch flow path after the blockage in the common path is removed.

In a preferred embodiment of the present invention, a plurality of electrolyte measuring electrodes and a hemoglobin measuring photometer are disposed in the first branch flow path, and a plurality of gas measuring electrodes and a hemoglobin measuring luminous intensity meter are disposed in the second branch flow path. The electrolyte measuring electrodes are apt to be affected by a pressure change in the flow path. A typical means for detecting the blockage of the flow path is a combination of a photocoupler and a timing mechanism, and this detecting means measures whether the sample has reached a position of the photocoupler within a predetermined time. As the timing mechanism, a microcomputer is used. In each of the branch flow paths, a flow path selector valve is provided to enable to introduce either a cleaning fluid or a standard liquid.

DETAILED DESCRIPTION

Figure 1:
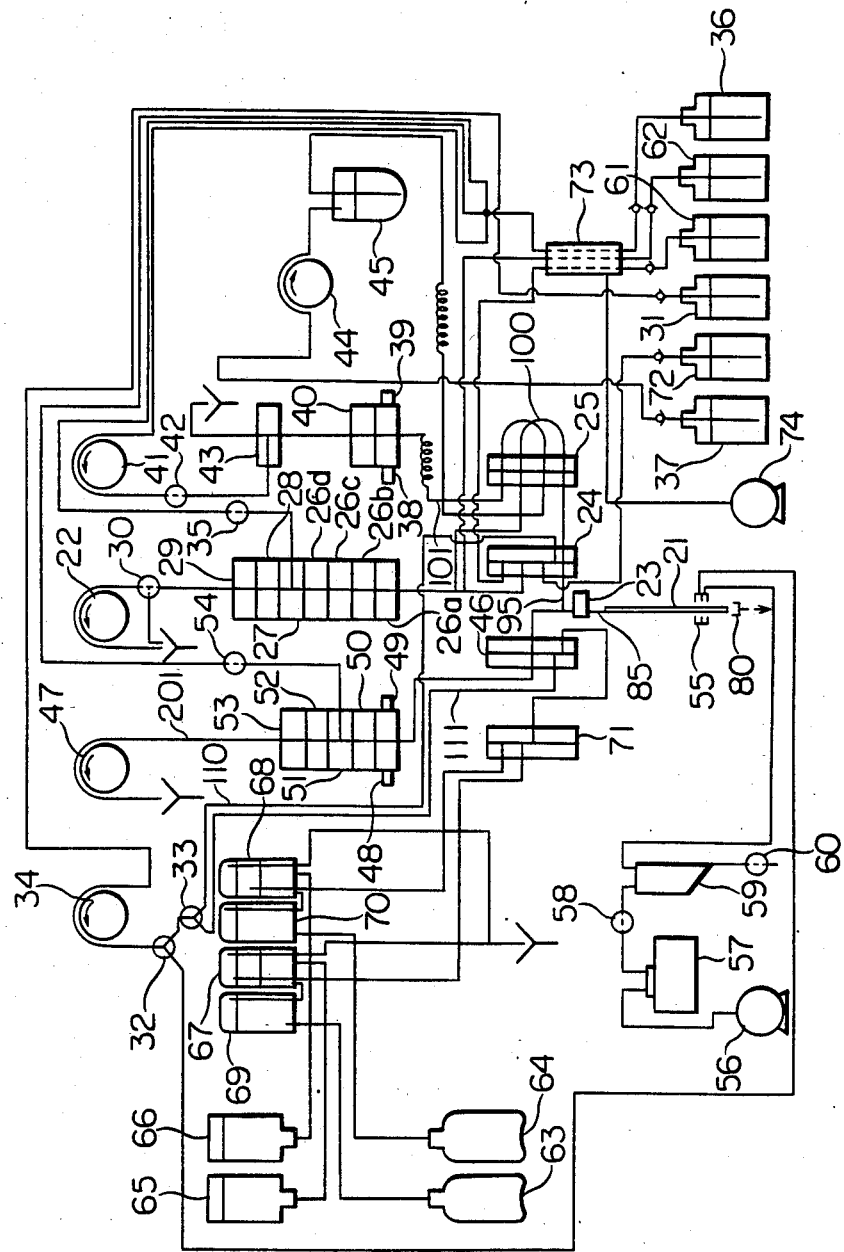
FIG. 1 is a flow path system diagram of an embodiment of the present invention.

An embodiment of the present invention will be described with reference to FIGS. 1 and 2. As shown in FIG. 2, an apparatus for analyzing multi-items is controlled with respect to the operation thereof by a microcomputer 11, and includes as an input/output section, a CRT display 12, a keyboard 13 and a printer 14, and includes as a storage medium 15, a floppy disk for storing analytical conditions, analysis results and the like. The microcomputer 11 controls connecting conditions of individual flow paths associated with a sample 90, calibrating standard liquids 61, 62, calibrating standard gases 67, 68, a buffer solution 37, and a cleaning fluid 31. Specifically, the operation of a pump and a selector valve provided in each flow path is controlled by the microcomputer 11.

In a first branch flow path, measuring electrodes including a sodium ion-measuring electrode 26a, a potassium ion-measuring electrode 26b, a chlorine ion-measuring electrode 26c, and a calcium ion-measuring electrode 26d which are not easily affected by a pressure change are disposed. In a second branch flow path, measuring electrodes including a carbon dioxide-measuring electrode 49, an oxygen-measuring electrode 48, and a pH-measuring electrode 50 which are apt to be affected by the pressure change are disposed. In a third branch flow path, a glucose-measuring electrode 38 and an urea/nitrogen-measuring electrode 39 which are electrodes for measuring biochemical components are disposed.

At the entry ports of the first and second branch flow paths, there are provided with valves respectively.

First, the valve of the first branch flow path is opened, and the blood sample is introduced into the flow path. In the first branch flow path, a blockage detector is disposed downstream of the electrolyte-measuring electrodes. When the sample does not reach the position of this detector within a predetermined time, the microcomputer 11 decides that the common path is blocked. In this case, the cleaning fluid 31 is supplied to the common flow path so that the cleaning fluid flows in a direction opposite to a flowing direction of the sample to thereby remove the blockage of the common path. Thereafter, the sample is introduced into the first branch flow path to reach a predetermined position, and the electrolyte components are measured. Following this, the valve of the second branch flow path is opened, and the blood sample is introduced into the second branch flow path. At this time, since the blockage of the common flow path has been removed, the pressure in the second branch flow path is never reduced abnormally.

Figure 2:
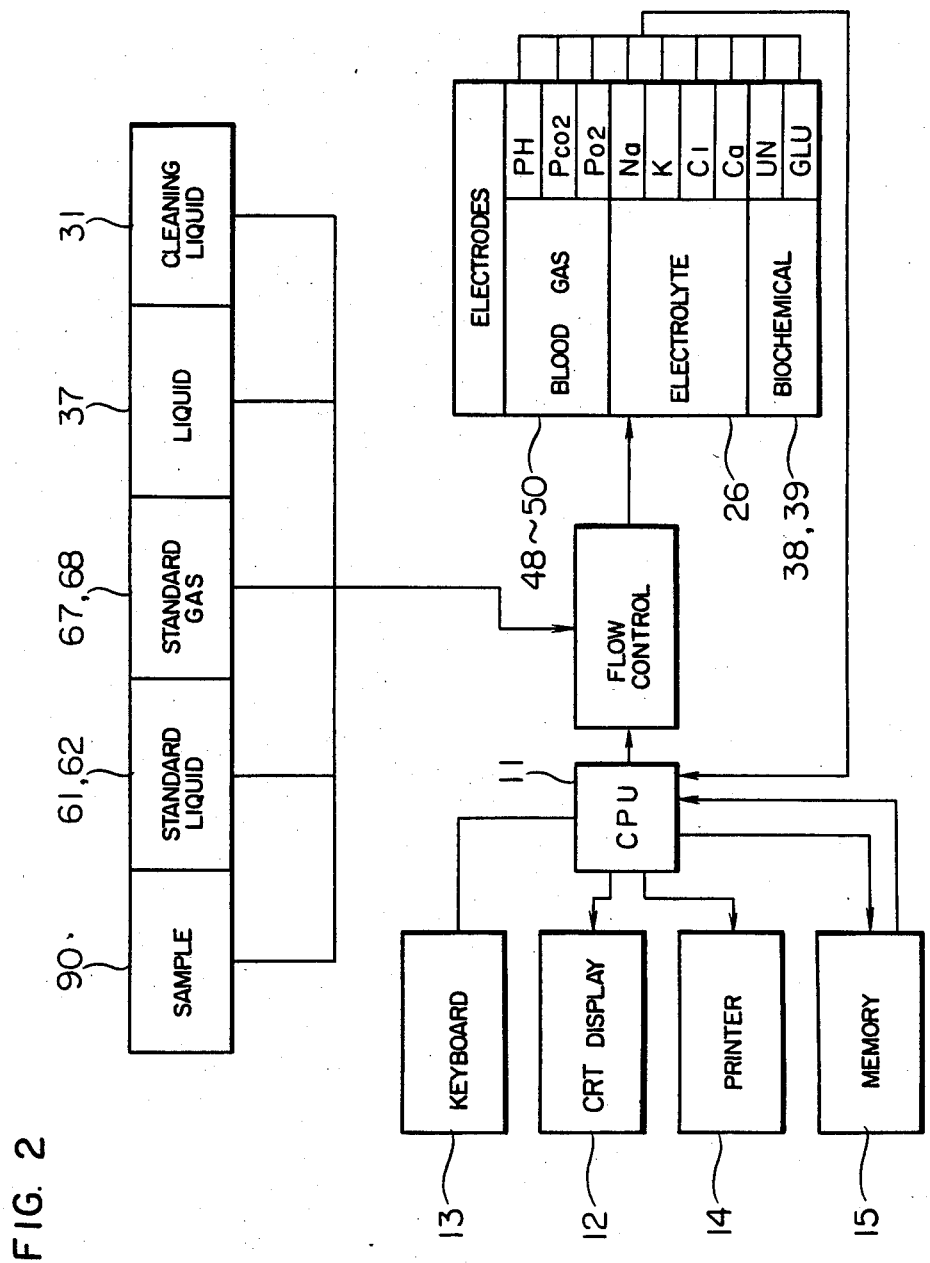
FIG. 2 is a system function diagram of the embodiment of FIG. 1.

An analyzing apparatus of FIG. 1 can be applied to either case in which the blood sample is contained in a test glass or in a syringe. In FIG. 1, a common flow path 85 has a sampling nozzle 21. A first branch flow path 95 passes through selector valves 24 and 25, a loop 100, measuring electrodes 26a to 26d, a reference electrode 27, a luminous intensity meter 28, a liquid detector 29, and a selector valve 30. A second branch flow path 201 passes through a selector valve 46, an oxygen measuring electrode 48, a carbon dioxide-measuring electrode 49, a pH-measuring electrode 50, a reference electrode 51, a luminous intensity meter 52, and a liquid detector 53.

When the blood sample is contained in the test glass, the tip of the sampling nozzle 21 is inserted into the test glass, and the sample is drawn into the common flow path 85 by the operation of a pump 22 in the first branch flow path. When the flow path is not blocked, the sample entering from the tip of the nozzle 21 reaches the position of the liquid sensor 29 through a liquid sensor 23, the selector valve 25, electrolyte-measuring electrodes 26a to 26b, reference electrode 27, and hemoglobin-measuring luminous intensity meter 28. Upon detection of the presence of the sample, the suction operation is stopped. As the liquid sensor 29, a well-known photocoupler may be used. Since the blood sample has a larger light absorbance than a carrier liquid (pure water), the presence of the sample is detected from a change in the amount of light absorption. The other liquid sensors 23, 40, and 53 are of a similar configuration.

When the sample does not reach the position of the liquid sensor 29 within the predetermined time even when the pump 22 is operated, since a signal indicative of the detection of the sample is not transmitted to the microcomputer, the microcomputer decides that the blockage is caused in the common flow path, and the pump 22 is stopped, and at the same time, a negative pressure in the first branch flow path is returned to the atmospheric pressure. Following this, the selector valve 24 is switched to make the common flow path 85 communicate with a flow path 110 which is connected to the cleaning fluid 31. Then, valves 32 and 33 are switched to the flow path 110, and a pump 34 is driven to feed the cleaning fluid to the flow path 110, and the cleaning fluid is discharged from the tip of the nozzle 21. This waste fluid is discharged through a waste fluid receiver 80. After the blockage is removed, the sample is drawn from the selector valve 24 until a beginning end of a band of the sample which has been at the upstream of the first branch flow path reaches the liquid sensor 29.

In both cases in which the blockage is removed and in which the blockage is not present, a valve 35 communicated with a reference liquid 36 is opened, and the selector valve 24 is closed, and the pump 22 is driven. Thus, the reference liquid 36 is introduced into the reference electrode 27. A potential difference between each potential of the sodium ion-measuring electrode 26a, potassium ion-measuring electrode 26b, chlorine ion-measuring electrode 26c, and calcium ion-measuring electrode 26d and a potential of the reference electrode 27 is measured, and concentration of each electrolyte component is calculated.

At this time, the selector valve 25 associated with a plurality of loops is switched so that a constant quantity of blood sample in a loop 100 is supplied by a pump 44 to pass through a flow path 101. A buffer solution 37 which is supplied by the pump 44 is smoothed by a damper 45, and the sample in the loop 100 is pushed out by the buffer solution 37. This sample is diffused in the flow path 101 and after being diluted, enters a blood sugar-measuring electrode or a glucose-measuring electrode 38 and an urea/nitrogen measuring electrode 39. When the beginning end of the sample band is detected by the liquid sensor 40, the pump 44 is stopped and the flow of the sample is stopped. Following this, a valve 42 communicated with the reference liquid 36 is opened, and the reference liquid 36 is supplied to a reference electrode 43 by driving a pump 41. A current value based on the glucose-measuring electrode 38 and a potential based on the urea/nitrogen measuring electrode 39 are measured, and the blood sugar concentration and the urea/nitrogen concentration are displayed.

On the other hand, the selector valve 46 which has been closed heretofore is switched, and by communicating a flow path of a pump 47 with the common flow path 85, the second branch flow path is formed. Thus, the blood sample in the test glass is introduced through the nozzle 21 to the position of the liquid sensor 23. In the case, in which no blockage is present in the common flow path 85 when the common flow path 85 is communicated with the first branch flow path, since the process of cleaning the common flow path 85 is eliminated, the blood sample remains in the common flow path 85. In this case, resampling by the nozzle 21 is not needed.

Following this, the pump 47 is driven, and the sample which has been in the common flow path 85 is introduced into the second branch flow path. The beginning end of a band of this sample is drawn until it reaches a liquid sensor 53 through the oxygen-measuring electrode 48, carbon dioxide-measuring electrode 49, pH-measuring electrode 50, reference electrode 51, and hemoglobine-measuring electrode 52. When the presence of the sample is dedected by the liquid sensor 53, the microcomputer 11 stops the operation of the pump 47. Next, the selector valve 46 is closed, and the valve 54 which is communicated with the reference liquid 36 is opened. Thereafter, the reference liquid 36 is supplied to the reference electrode 51 by driving the pump 47. After stopping the pump 47, potentials with respect to the pH-measuring electrode 50 and the carbon dioxide-measuring electrode 49 are measured, and a current with respect to the oxygen-measuring electrode 48 is measured. The measured values relating to these analysis items are displayed on the CRT display 12 and the printer 14.

A sampling method in which the blood sample is contained in the syringe will be described. In this case, the selector valves 24 and 25 are maintained so that the common flow path 85 is communicated with the electrolyte-measuring electrodes 26a to 26d, and the valve 30 is switched to a side opened to the atmosphere. When the pump 22 is stopped, the tip of the nozzle 21 is connected to a needle of the syringe, and the sample in the syringe is pressed into the flow path. In this case, when the sample reaches the liquid sensor 29, it is dealt with that the introduction of the sample has been completed normally, and the process thereafter is proceeded similarly to the measuring operation as described above.

As described above, when the analyzing operation is completed, in the analyzing apparatus, the cleaning operation is carried out. First, the inner wall of the nozzle 21 is cleaned. That is, the selector valve 24 is switched so that the flow path 110 is communicated with the common flow path 85, and the cleaning fluid 31 is supplied by the pump 34 to discharge the cleaning fluid from the tip of the nozzle 21. Next, the selector valve 46 is switched so that the flow path 111 is communicated with the common flow path 85, and further, the valve 33 is switched, and the cleaning fluid 31 supplied by the pump 34 is discharged from the tip of the nozzle 21.

Next, the outer wall of the nozzle 21 is cleaned. In this case, the nozzle cleaning fluid 31 is fed by the pump 34 through the valve 32 while a nozzle cleaning mechanism 55 is moved upwardly and downwardly, and at the same time, a vacuum pump 56 is operated to make a vacuum chamber 57 vacuum, and a valve 58 is opened by utilizing the vacuum to thereby draw the discharged fluid into a bottle 59, and preserved fluid is discharged through a valve 60.

In addition to the above-described steady state operation, the analyzing apparatus performs a calibration of the measuring electrodes over a constant time interval. In this case, when the electrolyte, blood sugar, and urea are used in place of the sample, a standard liquid 61 and another standard liquid 62 are alternately introduced into an electrolyte measuring flow path by the pump 22 and by switching the selector valve 24. Further, in the case of a blood gas, standard gases 63 and 64 are bubbled respectively through humidifiers 69 and 70 in bottles 67 and 68 containing standard liquids 65 and 66, respectively, and these two standard liquids are alternately switched by a selector valve 71 and introduced into a blood gas measuring flow path by the pump 47.

Further, the apparatus has an automatic cleaning function in which a sterilizing cleaning fluid 72 is introduced into the electrolyte measuring flow path through the selector valves 24 and 25 about once every day.

Each of the flow paths for the reference liquid 36, standard liquids 61 and 62 passes through a deaerator cylinder 73. These flow paths in the deaerator cylinder 73 are formed of porous plastic tubes. The pressure in the deaerator cylinder 73 is reduced by a pump 74. By this operation, air dissolved and preserved in each liquid is deaerated through the wall of each tube. Accordingly, even when these liquids are supplied to the flow paths in the analyzing apparatus, the generation of bubbles in the flow paths can be suppressed, and the measurement can be achieved without being affected by the bubbles for a long time.

We claim:

1. An apparatus of flow analysis comprising:
    a common flow path having a sample introducing nozzle;
    a plurality of branch flow paths each connected to said common flow path;
    means for detecting a flow path blockage, said means being disposed in a first branch flow path;
    means for removing the blockage by cleaning said common flow path when said flow path blockage is detected by said flow path blockage detecting means;
    a measuring electrode disposed in a second branch flow path, said measuring electrode being apt to be affected by a pressure change in the flow path; and
    means for introducing a sample into said second branch flow path after the blockage in said common flow path is removed.

2. An apparatus according to claim 1, wherein in said first branch flow path, a measuring electrode which is not easily affected by the pressure change in the flow path is disposed.

3. An apparatus according to claim 2, wherein said measuring electrode in said first branch flow path is an electrolyte measuring electrode, and said measuring electrode in said second branch flow path is a gas measuring electrode.

4. An apparatus according to claim 3 which further comprises means for supplying an electrolyte standard liquid in said first branch flow path and means for supplying a gas measuring standard liquid to said second branch flow path.

5. An apparatus according to claim 2, wherein in each of said first and second branch flow paths, a hemoglobin measuring photometer is disposed.

6. An apparatus according to claim 2 which further comprises a flow path for supplying a standard liquid toward the measuring electrode in said first branch flow path and a deaerating means for removing air in said standard liquid through a wall of said standard liquid supplying flow path.

7. A method of flow analysis, the method comprising the steps of:
    causing a common flow path to communicate with a first branch flow path by valve means, and shutting off a path between said common flow path and a second branch flow path by said valve means;
    introducing a liquid sample into said common flow path while said common flow path is communicating with said first branch flow path;
    measuring whether said liquid sample has reached a predetermined position in said first branch flow path from said common flow path within a predetermined time;
    cleaning said common flow path with a cleaning fluid when said liquid sample has not reached said predetermined position within said predetermined time;
    shutting off a path between said common flow path and said first branch flow path, and causing said common flow path to communicate with said second branch flow path; and
    introducing said liquid sample into said second branch flow path from said common flow path while said common flow path is communicating with said second branch flow path, and thereafter detecting a gas contained in said liquid sample with a gas measuring electrode disposed in said second branch flow path.

8. A method according to claim 7 wherein in said step of cleaning, a direction of flow of the cleaning fluid is opposite to a direction of introducing the sample.

9. A method according to claim 7 further comprising a step of cleaning an inner wall and an outer wall of said sample introducing section.

10. A method according to claim 7, wherein, in said step of detecting the gas, said liquid sample is brought into contact with said gas measuring electrode, and a reference liquid is supplied to a reference electrode disposed in said second branch flow path.

11. A method of flow analysis, the method comprising the steps of:
   causing a common flow path having a sample intake tube to communicate with a first branch flow path having a sample liquid detector and an electrolyte measuring electrode, and shutting off a path between said common path and a second branch flow path having a gas measuring electrode;
   introducing a liquid sample into said common flow path while said common flow path is communicating with said first branch flow path;
   measuring whether said liquid sample has reached a position of measurement by said sample detector in said first branch flow path from said common flow path within a predetermined time;
   cleaning said flow path with a cleaning fluid when said liquid sample has not reached said position of measurement within said predetermined time;
   following said cleaning step, introducing said liquid sample into said first branch flow path from said common flow path, and detecting ions contained in said liquid sample with said electrolyte measuring electrode;
   shutting off the path between said common flow path and said first branch flow path, and causing said common flow path to communicate with said second branch flow path; and
   introducing said liquid sample into said second branch flow path from said common flow path while said common flow path is communicating with said second branch flow path; and
   detecting a gas contained in said liquid sample with said gas measuring electrode.

12. An apparatus for flow analysis, the apparatus comprising:
   a common flow path provided with a sample intake tube;
   a first flow path disposed with a sample liquid detector;
   a second flow path disposed with a gas measuring electrode;
   means for supplying a cleaning liquid to said common path;
   valve means for causing said common flow path to communicate with or be shut off from said first flow path, for causing said common flow path to communicate with or be shut off from said second flow path, and for directing a flow of said cleaning fluid to said common flow path;
   control means for controlling said valve means so that said common flow path communicates with said first flow path and, at the same time, said common flow path is shut off from said second flow path for at least a predetermined time, said control means additionally controlling said cleaning liquid supplying means to supply the cleaning liquid when no signal is received from said sample liquid detector until a predetermined time period elapses, said control means further controlling said valve means so that said common flow path is shut off from said first flow path and, at the same time, said common flow path communicates with said second flow path after a liquid sample is introduced to a position of detection by said sample liquid detector;
   means for introducing said liquid sample into said second flow path from said common flow path while said common flow path is communicating with said second flow path; and
   means for displaying a result of a measurement of the gas based on a detection signal from said gas measuring electrode which detects the gas contained in said gas sample introduced into said second flow path.

13. An apparatus according to claim 12, wherein an electrolyte measuring electrode is further disposed in said first flow path.

14. An apparatus according to claim 13, wherein second valve means are disposed at a position downstream of said sample liquid detector and said electrolyte measuring electrode, and said second valve means opens said second flow path to the atmosphere.

* * * * *